(12) United States Patent
Ishikawa et al.

(10) Patent No.: US 8,572,933 B2
(45) Date of Patent: Nov. 5, 2013

(54) METHOD FOR MANUFACTURING SOFT CAPSULE AND APPARATUS FOR MANUFACTURING THE SAME

(75) Inventors: Nobuyuki Ishikawa, Fuji (JP); Koji Kajima, Fuji (JP); Yasunori Yamada, Fuji (JP); Tusue Akaike, Fujinomiya (JP)

(73) Assignee: Sankyo Co., Ltd., Fuji (JP)

( * ) Notice: Subject to any disclaimer, the term of this patent is extended or adjusted under 35 U.S.C. 154(b) by 300 days.

(21) Appl. No.: 13/119,631

(22) PCT Filed: Sep. 26, 2008

(86) PCT No.: PCT/JP2008/067407
§ 371 (c)(1),
(2), (4) Date: Mar. 17, 2011

(87) PCT Pub. No.: WO2010/035327
PCT Pub. Date: Apr. 1, 2010

(65) Prior Publication Data
US 2011/0162783 A1    Jul. 7, 2011

(51) Int. Cl.
*B65B 47/00*    (2006.01)
(52) U.S. Cl.
USPC .................................. 53/454; 53/900; 53/560
(58) Field of Classification Search
USPC ........................................... 53/454, 560, 900
See application file for complete search history.

(56) References Cited

U.S. PATENT DOCUMENTS

| | | | |
|---|---|---|---|
| 2,590,186 A * | 3/1952 | Land ............................. | 427/369 |
| 4,656,066 A * | 4/1987 | Wittwer ...................... | 428/34.1 |
| 4,894,978 A * | 1/1990 | Schonmann et al. ........... | 53/560 |
| 5,342,626 A | 8/1994 | Winston, Jr. et al. | |
| 6,006,368 A * | 12/1999 | Phillips ............................. | 2/468 |
| 6,101,735 A * | 8/2000 | Kuhasalo et al. ............... | 34/117 |
| 6,214,376 B1 | 4/2001 | Gennadios | |
| 6,295,793 B1 * | 10/2001 | Takayanagi ..................... | 53/454 |

(Continued)

FOREIGN PATENT DOCUMENTS

| | | |
|---|---|---|
| JP | B2-05-088143 | 12/1993 |
| JP | A-06-329833 | 11/1994 |

(Continued)

OTHER PUBLICATIONS

Japanese Office Action issued in Japanese Patent Application No. 2010-530658 dated Jun. 28, 2011.

(Continued)

*Primary Examiner* — Alexandra Elve
*Assistant Examiner* — Eyamindae Jallow
(74) *Attorney, Agent, or Firm* — Oliff & Berridge, PLC

(57) ABSTRACT

An apparatus for manufacturing a soft capsule containing a filling coated with a shell portion formed of a shell-sheet, having a sheet molding section forming a shell-sheet having an almost uniform thickness from a molten shell material, a capsule molding section feeding shell-sheets between a pair of die rolls and joining the shell sheets, and a filling supply section supplying a filling to the shell-sheets in time for joining the shell-sheets, in which the sheet molding section has a dryer equipped with a medium wavelength infrared heater; the shell-sheet is irradiated with a medium wavelength infrared ray from the heater to thereby obtain an almost uniform thickness, an appropriate viscosity, and moisture content; and the sheet of this state is fed to the capsule molding section.

14 Claims, 8 Drawing Sheets

(56) References Cited

U.S. PATENT DOCUMENTS

| | | | |
|---|---|---|---|
| 6,402,496 B2* | 6/2002 | Ishikawa et al. | 425/116 |
| 6,755,010 B2* | 6/2004 | Draisey | 53/454 |
| 6,949,256 B2* | 9/2005 | Fonkwe et al. | 424/451 |
| 7,490,456 B2* | 2/2009 | Draisey et al. | 53/560 |
| 7,887,838 B2* | 2/2011 | Archibald et al. | 424/452 |
| 2002/0026771 A1* | 3/2002 | Brown | 53/454 |
| 2002/0081331 A1 | 6/2002 | Tanner et al. | |
| 2002/0134055 A1* | 9/2002 | Martinez, Jr. | 53/454 |
| 2003/0014946 A1* | 1/2003 | Steele et al. | 53/454 |
| 2004/0060258 A1* | 4/2004 | Stolz | 53/266.1 |
| 2005/0019374 A1* | 1/2005 | Modliszewski et al. | 424/439 |
| 2005/0191346 A1 | 9/2005 | Nowak et al. | |
| 2006/0096252 A1* | 5/2006 | Nakamura et al. | 53/454 |
| 2008/0307753 A1* | 12/2008 | Kessel | 53/454 |

FOREIGN PATENT DOCUMENTS

| | | |
|---|---|---|
| JP | 8-169817 A | 7/1996 |
| JP | A-2003/040768 | 2/2003 |
| JP | A-2003-504326 | 2/2003 |
| JP | A-2003-521287 | 7/2003 |
| JP | A-2005-112849 | 4/2005 |
| JP | 2006-096695 A | 4/2006 |
| JP | A-2008-237572 | 10/2008 |
| WO | WO 01/03676 A1 | 1/2001 |
| WO | WO 01/03677 A1 | 1/2001 |
| WO | WO 2006/121098 | 11/2006 |

OTHER PUBLICATIONS

Miyamoto et al., "New Development of Natural Biopolymer Material," 2003, pp. 62-69, CMC Publishing Co., Ltd. (with abstract).

"Gelatinization Properties," Chuo Foods Material Co., Ltd., 2002, <http://www.chuofoods.co.jp/jgc03.html> (with abstract).

"Outline of Carrageenan," FMC Biopolymer Department, pp. 4-8 (with abstract).

International Search Report issued in corresponding International Application No. PCT/JP2008/067407 dated Dec. 9, 2008 (with translation).

* cited by examiner

METHOD FOR MANUFACTURING SOFT CAPSULE AND APPARATUS FOR MANUFACTURING THE SAME

TECHNICAL FIELD

The present invention relates to a process for manufacturing a soft capsule generally and widely used for "medical products", "specially designated health foods", "so-called health foods", and foods, and particularly relates to a method for manufacturing a soft capsule having a shell portion mainly using a vegetable material, i.e., starch, instead of using an animal material, i.e., gelatin, and an apparatus for manufacturing the same.

BACKGROUND ART

Soft capsules, which contains gelatin produced from bone and skin of cows and pigs, as a main component, and which are produced by a rotary die system automatic soft capsule manufacturing machine, have conventionally been widely used in the fields of "medical products" and "so-called health foods".

However, since occurrence of BSE (Bovine Spondiform Encepralopany) was recently reported, attention has been focused on development of soft-capsule shell using a non-animal derived material instead of using animal-derived gelatin.

In the circumstance, Patent Documents 1 and 2 disclose an encapsulation technique using a combination of carrageenan gum and mannan gum as a gelatinizer without using gelatin. Also, Patent Document 3 discloses an encapsulation technique using κ carrageenan. Furthermore, Patent Document 4 discloses a technique on capsules using τ carrageenan and κ carrageenan. Moreover, Non-Patent Document 3 discloses that λ carrageenan provides high viscosity but does not turn into a gel.

As the properties of τ carrageenan and κ carrageenan, Non-Patent Document 1 describes "when κ- or τ-carrageenan is dispersed in water and heated to about 60° C. or more, a carrageenan molecule is dissolved in the form of a random coil. The solution is continuously cooled to form a double helix. This serves as a junction zone and then gelatinization starts". Due to such a property, when an encapsulation film is formed using τ carrageenan and κ carrageenan, the encapsulation film sheet must be heated at a temperature higher by about at least 20 to 30° C. than the temperature of the case where gelatin is used as an encapsulation film. Because of this, a large heat load is applied to a capsule filling. This causes a problem in quality and lowers the efficiency of heat energy.

Under the circumstances, the present inventors noticed that if an encapsulation film can be formed by using λ carrageenan (see Non-Patent Document 2 and Non-Patent Document 3) which does not turn to a gel unlike κ carrageenan and τ carrageenan, encapsulation can be made without applying heat load to a capsule filling just by applying the same level of temperature as in a conventional gelatin sheet (temperature of a segment section: usually 35 to 50° C.) to an encapsulation film sheet, and advantageously improves heat energy efficiency. Then, the present inventors conducted inventive studies by themselves and successfully developed a soft capsule having a non-animal derived shell portion (capsule shell) using starch, λ carrageenan, a metal salt, dextrin, plasticizer, and water, and filed a patent application (Japanese Patent Application No. 2007-082542) in advance. Note that, since the prior patent application "Japanese Patent Application No. 2007-082542" was not published at the time this patent application was filed, this was not conventional art.

However, in a method for manufacturing a soft capsule having a non-animal derived capsule shell using starch, λ carrageenan, a metal salt, dextrin, a plasticizer, and water by means of a conventional rotary die system automatic soft capsule manufacturing machine (for example, Patent Documents 5 and 6), since drying capacity in a step of manufacturing a non-animal derived capsule shell-sheet is insufficient, dry load must be reduced by reducing a moisture content of a capsule shell solution.

However, if the moisture content is reduced, it becomes difficult to remove air incorporated in the capsule shell solution in a defoaming step. Visible air foams remain in the capsule shell-sheet. In short, a capsule having a defoaming defect is formed. This is a problem.

Furthermore, even if a conventional rotary die system automatic soft capsule manufacturing machine is used and dry load is reduced by reducing a blending ratio of moisture content, it must take time to supply a highly viscose capsule shell solution. When a rate of filling a soft capsule is increased, neither drying capacity in the capsule shell-sheet manufacturing step nor supply of the capsule shell solution fails to follow, preventing improvement of productivity.

Patent Document 1: U.S. Pat. No. 5,342,626
Patent Document 2: Japanese Patent Laid-Open No. 6-329833
Patent Document 3: U.S. Pat. No. 6,214,376
Patent Document 4: National Publication of International Patent Application No. 2003-504326
Patent Document 5: Japanese Patent Publication No. 5-88143 (cooling drum)
Patent Document 6: Japanese Patent Laid-Open No. 2003-40768 (servo)
Non-Patent Document 1: "New development of natural biopolymer material" edited by Takeaki Miyamoto et al., CMC publishing Co., Ltd, popular edition first copy issued on Nov. 28, 2003, pages 64 to 65.
Non-Patent Document 2: Chuo Foods Material Co., Ltd., "Home Page of Chuo Foods Material Co., Ltd.", [onlion], "contents of a corporation (2002)"→"carrageenan"→"properties of carrageenan"→section of "gelatinization properties" [searched on Jan. 30, 2007], Internet <URL http://www-.chuofoods.co.jp/jgc03.html>
Non-Patent Document 3: FMC biopolymer department, "outline of carrageenan" pages 6 to 7

DISCLOSURE OF THE INVENTION

Problems to be Solved by the Invention

The present invention was attained in consideration of the aforementioned background.

More specifically, an object of the present invention is to develop a novel method for producing a capsule, which is capable of freely controlling the moisture content of the capsule shell-sheet by incorporating a process for drying a capsule shell-sheet with medium wavelength infrared irradiation into a conventional rotary die system automatic soft capsule manufacturing process to augment drying capacity. By virtue of this, there are provided a novel manufacturing method and apparatus, which is not only capable of drying a capsule shell-sheet adhesion surface uniformly to an appropriate moisture content in a conventional production of a soft capsule containing gelatin, a plasticizer, and water as a main component, but also, capable of drying a capsule shell-sheet adhesion surface uniformly without irregularity to an appropriate moisture content, in production of a soft capsule having a non-animal derived capsule shell using starch, λ carrageenan, a metal salt, dextrin, a plasticizer, and water, even if a capsule shell solution whose viscosity is reduced by increasing the moisture content (90 to 160 parts by weight relative to starch (100 parts by weight)) in order to improve a defoaming property and flowability of the capsule shell solution is supplied, thereby improving productivity, such as prevention of a defoaming defect of a capsule and an increase of a capsule fill rate, cost performance, and quality.

Means for Solving the Problems

First, the method for manufacturing a soft capsule according to aspect of the invention is a method for manufacturing a soft capsule containing a filling within a shell portion formed of a shell-sheet by supplying shell-sheets between a pair of die rolls so as to face each other, joining the shell-sheets by butt joint function of the die rolls, supplying the filling between the shell-sheets in time for joining, in which the shell-sheets are dried by irradiation of a medium wavelength infrared ray before they are joined by the pair of die rolls, thereby turning into a sheet-form having an almost uniform thickness, an appropriate viscosity, and moisture content.

Furthermore, the method for manufacturing a soft capsule according to another aspect of the invention is characterized in that, in addition to the features previously described, the shell portion is formed by blending starch, λ carrageenan, metal salt, dextrin, a plasticizer, and water as components for a raw material composition.

Furthermore, the method for manufacturing a soft capsule according to another aspect of the invention is characterized in that, in addition to the features previously described, the wavelength of the medium wavelength infrared ray to be applied for drying the shell-sheet is 0.8 to 4.0 μm.

Furthermore, the method for manufacturing a soft capsule according to another aspect of the invention is characterized in that, in addition to the features according to the features previously described, the shell-sheet is dried by medium wavelength infrared irradiation up to a moisture content of preferably 19 to 29% and more preferably 21 to 27% at a stage of feeding between the pair of die rolls.

Furthermore, the method for manufacturing a soft capsule according to another aspect of the invention is characterized in that, in addition to the features previously described, the shell-sheet is dried by medium wavelength infrared irradiation in at least two stages, and both surfaces of the shell-sheet are dried by irradiating one of the surfaces of the shell-sheet separately in each stage.

Furthermore, the method for manufacturing a soft capsule according to another aspect of the invention is characterized in that, in addition to the features previously described, the shell portion in a liquid state before drying is set to have a moisture content of 90 to 160 parts by weight relative to 100 parts by weight of starch.

Furthermore, the method for manufacturing a soft capsule according to another aspect of the invention is characterized in that, in addition to the features previously described, the shell portion in a liquid state before drying contains 5 to 25 parts by weight of λ carrageenan, 0.5 to 10 parts by weight of a metal salt, 3 to 100 parts by weight of dextrin, 20 to 80 parts by weight of a plasticizer, and 90 to 160 parts by weight of water relative to 100 parts by weight of starch.

Furthermore, the method for manufacturing a soft capsule according to another aspect of the invention is characterized in that, in addition to the features previously described, further contains κ carrageenan and τ carrageenan so as to satisfy a ratio of λ carrageenan: κ carrageenan: τ carrageenan=1:0.1:0.1 to 1:0.8:0.2.

More specifically, the invention of Claim 8 is characterized in that if κ carrageenan and τ carrageenan are contained, the working effect of a metal salt added to λ carrageenan is not inhibited.

The apparatus for manufacturing a soft capsule according to another aspect of the invention is an apparatus for manufacturing a soft capsule containing a filling coated with a shell portion formed of a shell-sheet, configured to have a sheet molding section forming the shell-sheet having an almost uniform thickness from a molten shell material, a capsule molding section joining shell-sheets supplied between a pair of die rolls so as to face each other by butt joint function of the pair of die rolls having a molding projection, and a filling supply section supplying a filling to the shell-sheets in time for joining the shell-sheets, in which the sheet molding section has a dryer equipped with a medium wavelength infrared heater; the shell-sheets are irradiated with a medium wavelength infrared ray from the heater to thereby obtain an almost uniform thickness, an appropriate viscosity, and moisture content; and the sheets of this state are fed to the capsule molding section.

Furthermore, the apparatus for manufacturing a soft capsule according to another aspect of the invention is characterized in that, in addition to features of the apparatus previously described, the wavelength of the medium wavelength infrared ray applied from the medium wavelength infrared heater of the dryer to the shell-sheet is 0.8 to 4.0 μm.

Furthermore, the apparatus for manufacturing a soft capsule according to another aspect of the invention is characterized in that, in addition to the features of the apparatus previously described, the sheet molding section is configured to have a spreader box, in which a molten shell material is ejected in a sheet form having an almost uniform thickness, and a casting drum, in which the shell-sheet ejected from the spreader box is cooled, and drying of the shell-sheet by the dryer includes single-sided drying, in which one of the surfaces of the shell-sheet positioned on the casting drum is irradiated with a medium wavelength infrared ray to thereby dry mainly the one surface of the shell-sheet, and double-sided drying, in which the shell-sheet is removed from the casting drum and taken out in a transport path, in which a medium wavelength infrared ray is separately applied to each of the surfaces to thereby dry both surfaces of the shell-sheet, and each one or both of the single-sided drying and the double-sided drying are employed.

Furthermore, the apparatus for manufacturing a soft capsule according to another aspect of the invention is characterized in that, in addition to the features of the apparatus previously described, when double-sided drying is performed by taking out the shell-sheet separately from the casting drum to the transport path and supplying air toward the irradiation surface of the shell-sheet from the upstream side to the downstream side in the sheet transport direction and a support is provided so as to support the shell-sheet from below.

The present inventors previously found that when a predetermined amount of metal salt is added to λ carrageenan, which does not turn to a gel, to obtain a weak acidic condition, λ carrageenan acquires an appropriate viscosity and elasticity to obtain a preferable composition for forming a soft capsule. Based on the finding, the inventors accomplished a non-animal derived capsule shell using a vegetable material that has not been developed in the art and a soft capsule having the shell.

Furthermore, a process for drying a capsule shell-sheet with medium wavelength infrared irradiation is incorporated in a general rotary die system automatic soft capsule manufacturing process to augment drying capacity, thereby freely controlling the moisture content of a capsule shell-sheet. In this manner, the inventors have developed a novel capsule manufacturing process and attained the present invention.

According to a process for manufacturing a soft capsule of the present invention, not only, in producing a conventional soft capsule containing gelatin, a plasticizer, and water as main components, a capsule shell-sheet adhesion surface can be uniformly dried up to an appropriate moisture content, but also, in producing a soft capsule having a non-animal derived capsule shell using starch, $\lambda$ carrageenan, a metal salt, dextrin, a plasticizer, and water, even if a capsule shell solution whose viscosity is reduced by increasing the moisture content (90 to 160 parts by weight relative to starch (100 parts by weight)) in order to improve a defoaming property and flowability of the capsule shell solution is supplied, the adhesion surface of the capsule shell-sheet can be uniformly dried without irregularity to an appropriate moisture content, thereby improving productivity such as prevention of a defoaming defect of a capsule and an increase of a capsule fill rate, cost performance, and quality.

The shell portion of the non-animal derived soft capsule manufactured by the soft capsule manufacturing apparatus of the present invention is formed of a composition containing starch, $\lambda$ carrageenan, a metal salt, dextrin, a plasticizer, and water as components, the moisture content of a shell in the state of liquid before drying (in the state of a solution before the shell portion is dried) is preferably 90 to 160 parts by weight, more preferably 95 to 150 parts by weight, and particularly preferably 100 to 140 parts by weight relative to 100 parts by weight of starch. The moisture content of 90 parts by weight or less is not preferable because air incorporated in a highly viscous capsule shell solution is hardly removed, meaning that air is not sufficiently defoamed in the defoaming step. As a result, a defoaming-defective capsule having foams in the capsule shell-sheet tends to be formed. In addition, flowability of the capsule shell solution deteriorates, preventing an increase of a capsule fill rate. On the other hand, the moisture content of 160 parts by weight or more is not preferable because the capsule shell-sheet becomes too soft to remove it from the casting drum.

The viscosity of a solution containing a moisture content of 90 to 160 parts by weight relative to 100 parts by weight of starch (not containing $\lambda$ carrageenan, a metal salt, dextrin, and a plasticizer) is 3000 to 13000 cps (low viscosity) as measured in a 10% concentration of the solution at 75° C. after the solution is dissolved at a temperature of 85 to 95° C. for 6 hours.

On the other hand, the viscosity of a solution containing a moisture content of 60 to 90 parts by weight relative to 100 parts by weight of starch (not containing $\lambda$ carrageenan, a metal salt, dextrin, and a plasticizer) is 13000 to 35000 cps (high viscosity) as measured in a 10% concentration of the solution at 75° C. after the solution is dissolved at a temperature of 85 to 95° C. for 6 hours. Note that, viscosity was measured by a Type B viscometer manufactured by Tokimec.

The metal salt, which is a component constituting the shell portion of the non-animal derived soft capsule manufactured by the soft capsule manufacturing apparatus of the present invention, is an organic acid metal salt such as sodium succinate, potassium citrate, and sodium gluconate, and a combination of one or two or more inorganic metal salts selected from the group consisting of disodium hydrogen-phosphate, sodium dihydrogen phosphate, potassium chloride, and magnesium chloride. Of them, a combination of sodium dihydrogen phosphate and potassium chloride is preferably used.

As the blending ratio of a metal salt, 1 to 3 parts by weight of sodium dihydrogen phosphate and 0.05 to 0.2 parts by weight of chloride potassium are preferably used relative to 100 parts by weight of starch in a shell solution state (in the state of a solution before the shell portion is dried) before drying. Further preferably, sodium dihydrogen phosphate is 1.5 to 2.5 parts by weight and chloride potassium is 0.08 to 0.12 parts by weight. If sodium dihydrogen phosphate is 1 part by weight or less, $\lambda$ carrageenan fails to provide an appropriate viscosity and elasticity, with the result that a preferable soft capsule cannot be formed. On the other hand, sodium dihydrogen phosphate of 3 parts by weight or more is not preferable since $\lambda$ carrageenan may possibly be hydrolyzed.

[Working Effect of Metal Salt Addition]

The present inventors found that addition of a predetermined amount of metal salt to $\lambda$ carrageenan which does not turn to a gel imparts an appropriate viscosity and elasticity to the $\lambda$ carrageenan. The working effect of the metal salt addition is not completely elucidated; however, herein, the working effect of a case where sodium dihydrogen phosphate and potassium chloride are added will be described as an example. Note that, the non-animal derived soft capsule manufactured by the soft capsule manufacturing apparatus of the present invention is not limited to this example. Even if $\kappa$ carrageenan and $\tau$ carrageenan are contained, the working effect of the metal salt addition to $\lambda$ carrageenan is not inhibited.

(1) Function of a Weak Acidic Metal Salt such as Sodium Dihydrogen Phosphate $\lambda$ carrageenan is an anionic polymer. Thus if it is dissolved in the presence of a cationic ion ($H^+$, $Na^+$), $\lambda$ carrageenan becomes transparent. When a weak acidic metal salt such as sodium dihydrogen phosphate is added to the anionic polymer, i.e., $\lambda$ carrageenan, an appropriate viscosity (adhesiveness) is obtained without causing hydrolysis.

(2) Function of a Metal Salt such as Chloride Potassium and Potassium Citrate

By supplying $K^+$ (potassium ion), for example, by chloride potassium, to an anionic polymer, $\lambda$ carrageenan, under weak acidic conditions, an anionic polymer, $\lambda$ carrageenan, forms a complex or the like around $K^+$, enhancing elasticity.

(3) Function of Starch

Since a sheet is in a molten state having an appropriate viscosity (adhesiveness) and elasticity and gelatinized starch has a sealing property by gelatinization, a soft capsule is formed by (i) pressure-molding using a mold (die roll described later) and (ii) welding by starch glue.

The property of $\kappa$ carrageenan and $\tau$ carrageenan is described in Non-Patent Document 1 mentioned above, as follows: "when $\kappa$- or $\tau$-carrageenan is dispersed in water and heated to about 60° C. or more, the carrageenan molecule is dissolved in the form of a random coil. The solution is continuously cooled to form a double helix. This serves as a junction zone and then gelatinization starts". Due to such a property, when an encapsulation film is formed from $\tau$ carrageenan and $\kappa$ carrageenan, the encapsulation film sheet must be heated at a temperature higher by about at least 20 to 30° C. than the temperature (segment section temperature: usually 35 to 50° C.) of the case where an encapsulation film is formed from gelatin. Because of this, a large heat load is applied to a capsule filling. This causes a problem in quality and poor heat energy efficiency.

However, the present inventors found that addition of a predetermined amount of metal salt to λ carrageenan which does not turn to a gel imparts an appropriate viscosity and elasticity to the λ carrageenan, and accomplished a non-animal derived soft capsule. Therefore, unlike κ carrageenan and τ carrageenan, when an encapsulation film is formed of λ carrageenan, encapsulation can be performed at about the same segment section temperature as that (segment section temperature: usually 35 to 50° C.) of the case where gelatin is used, without applying excessive heat load to a capsule filling. Good heat energy efficiency is advantageously obtained.

As starch, which is a component of the shell portion of the non-animal derived soft capsule manufactured by the soft capsule manufacturing apparatus of the present invention, one or two or more elements selected from raw starch, HP treated starch, acid treated starch, and gelatinized starch (α-starch) are used singly or in combination of two or more types.

A starch derivative, i.e., HP treated starch, used herein is starch treated with hydroxypropyl ether. Any HP treated starch can be used as long as it is commercially available. For example, TR-3 (trade name) manufactured by Tokai Denpun Co., Ltd., Mastutani Yuri (trade name), Finex 600 (trade name) manufactured by Matsutani Chemical Industry Co., Ltd., and Delica KH (trade name) manufactured by Nippon Starch Chemical Co., Ltd. can be used. Another starch derivative, α-starch, is a starch soluble in cold water and capable of being gelatinized (soluble) at normal temperature. For example, tapioca α-TP-2 (trade name) manufactured by Sanwa Cornstarch Co., Ltd. can be used.

The plasticizer, which is a component of the shell portion of the non-animal derived soft capsule manufactured by the soft capsule manufacturing apparatus of the present invention, includes glycerin, sugar alcohol, propylene glycol, polyethylene glycol, a monosaccharide, a disaccharide, an oligosaccharide, and isomaltooligosaccharide. The blending ratio of a plasticizer in a shell solution state before drying is 20 to 80 parts by weight and more preferably 40 to 70 parts by weight relative to 100 parts by weight of starch.

Advantages of the Invention

The present inventors previously found that when a predetermined amount of metal salt is added to λ carrageenan which does not turn to a gel to obtain a weak acidic condition, λ carrageenan acquires an appropriate viscosity and elasticity to obtain a preferable composition for forming a soft capsule. Based on the finding, the inventors accomplished a non-animal derived capsule shell using a vegetable material that has not been developed and a soft capsule having the shell.

Furthermore, the inventors have developed a novel method for producing a soft capsule, which is capable of freely controlling the moisture content of a capsule shell-sheet by incorporating a process for drying a capsule shell-sheet with medium wavelength infrared irradiation into a rotary die system automatic soft capsule manufacturing process to augment drying capacity, and have attained the present invention.

According to the process for manufacturing a soft capsule of the present invention, not only, in producing a conventional soft capsule containing gelatin, a plasticizer, and water as main components, a capsule shell-sheet adhesion surface can be uniformly dried up to an appropriate moisture content, but also, in producing a soft capsule having a non-animal derived soft capsule shell using starch, λ carrageenan, a metal salt, dextrin, a plasticizer, and water, even if a capsule shell solution whose viscosity is reduced by increasing the moisture content (90 to 160 parts by weight relative to starch (100 parts by weight)) thereof to improve a defoaming property and flowability of the capsule shell solution is supplied, the adhesion surface of the capsule shell-sheet can be uniformly dried without irregularity to appropriate moisture content, thereby improving productivity such as prevention of a defoaming defect of a capsule and an increase of a capsule fill rate, cost performance and quality.

DESCRIPTION OF SYMBOLS

Figure 1:
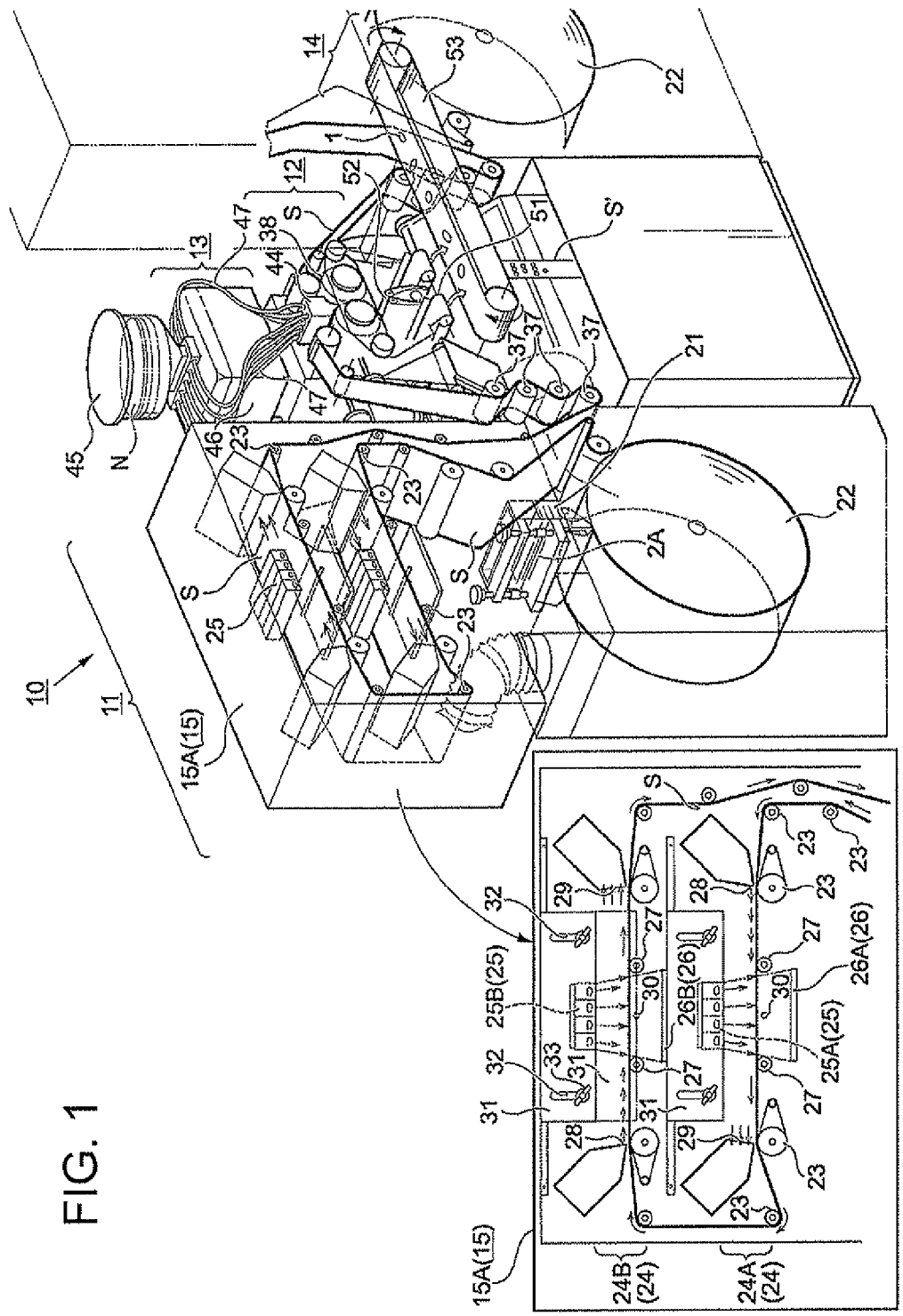
FIG. 1 is a perspective view of an apparatus (filling machine) for manufacturing a soft capsule of the present invention together with an explanatory view of a dryer having a medium wavelength infrared irradiation mechanism, as viewed from the front.

1 Soft capsule
2 Shell portion
2A Shell material
10 Soft capsule manufacturing apparatus (filling machine)
11 Sheet molding section
12 Capsule molding section
13 Filling supply section
14 Capsule take-out section
15 Dryer
15A Dryer main body
21 Spreader box
22 Casting drum
23 Feed role
24 Transport path
24A Transport path (front surface side)
24B Transport path (back surface side)
25 Medium wavelength infrared heater
25A Medium wavelength infrared heater (front surface side)
25B Medium wavelength infrared heater (back surface side)
29 Reflecting plate
26A Reflecting plate (front surface side)
26B Reflecting plate (back surface side)

27 Support
28 Air spray member
29 Air suction member
30 Thermometer
31 Cover
32 Slit
33 Wing bolt
34 Cover
37 Feed role
38 Die roll
39 Molding recess
40 Molding projection
41 Suction hole
44 Segment
45 Raw-material solution hopper
46 Pump unit
47 Delivery pipe
50 Scraping brush
51 Forward conveyer
52 Free roller
53 Conveyer
N Filling
P Pocket portion
S Shell-sheet
S' Blank sheet

BEST MODE FOR CARRYING OUT THE INVENTION

The best mode for carrying out the present invention is one of the Embodiments described below, and further includes various processes that can be improved within the technical idea thereof.

Note that, in the beginning of the explanation, a basic structure of a soft capsule 1 according to the present invention will be described and then, an apparatus (the apparatus of the present invention) for manufacturing the soft capsule 1 will be described. Subsequently, while describing how to operate the apparatus, a method of manufacturing a soft capsule according to the present invention will be described. Furthermore, the method of the present invention will be more specifically explained by showing a component composition of a capsule shell actually used.

[Basic Structure of Soft Capsule]

Figure 4:
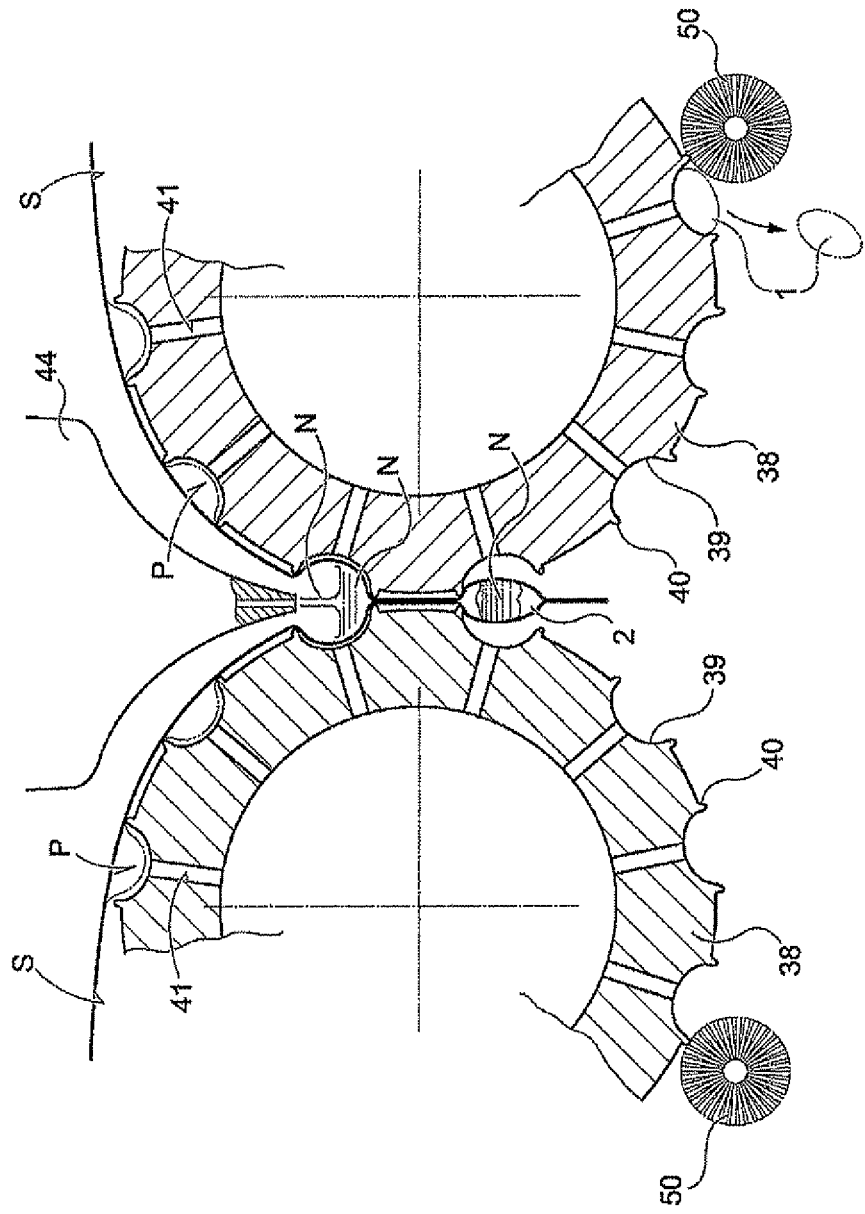
FIG. 4 is a front view of a pair of die rolls by which a soft capsule is manufactured.

A basic structure of the soft capsule 1 is, for example, as shown, in FIG. 4, formed by coating a filling N such as a medicinal solution with a shell portion 2.

The filling N herein, other than a medical product, desired materials such as food, a seasoning (seasoning oil), a cosmetic, a bath article, and a miscellaneous good (e.g., a toy/adhesive) can be appropriately used. Furthermore, the state of the filling encapsulated (accommodation state) can be a liquid as well as a gel, a particulate matter, or an appropriate mixture of these, for example, a powder-containing suspension solution having a powder mixed in a liquid. Note that, in the following explanation, the case of containing a liquid-state filling N will be principally described.

On the other hand, the shell portion 2 can be formed of animal-derived gelatin as a base like a conventional case; however, herein, formed of a plant-derived starch as a main component, as described above, more specifically formed of starch, λ carrageenan, a metal salt, dextrin, a plasticizer, and water. Note that specific compositions of these components will be described later.

[Manufacturing Apparatus]

Next, a soft capsule manufacturing apparatus 10 (hereinafter simply referred to as a filling machine 10) for manufacturing the soft capsule 1 will be described. As the filling machine 10, a conventional rotary die system automatic soft capsule manufacturing machine can be used as it is. The filling machine 10, for example, as shown in FIG. 1, is configured to have a sheet molding section 11 forming a molten shell material (designated as reference numeral 2A since this is a raw material for forming a shell portion 2) while drying into a sheet-form having an appropriate thickness, a capsule molding section 12 joining molded shell-sheets S so as to face each other, thereby encapsulating the filling N within the shell-sheets 8, a filling supply section 13 feeding the filling N in time for joining of the shell-sheets S, and a capsule taking out section 14 taking out the soft capsule 1 formed, from the filling machine 10. Note that, the present invention has a great feature in that a dryer 15 having a medium wavelength infrared irradiation mechanism, which is provided in the sheet molding section 11, thereby drastically improving drying capacity compared to a conventional manufacturing method. Hereinafter, individual sections will be described.

In the first place, the sheet molding section 11 will be described. This is a section at which the molten shell material 2A is solidified into a sheet form. To supply the two shell-sheets S molded to a junction (a pair of die rolls) so as to face each other, for example, a pair of sheet molding sections 11 are provided on the right and left side of the capsule molding section 12 such that the section 12 is sandwiched.

The sheet molding section 11 is configured to have a spreader box 21, in which the molten shell material 2A is ejected in the form of sheet having an almost uniform thickness and a casting drum 22 for cooling the shell-sheet S ejected from the spreader box 21. The shell-sheet S is formed into a sheet form having an appropriate thickness while being cooled to an appropriate temperature. Note that, a process for dissolving the shell material 2A will be described later.

The dryer 15 above will be described. The dryer 15 is used for drying the shell-sheet S, which is formed by solidifying the shell material 2A into a sheet form, is dried and adjusted to a desired moisture content. Note that, the reason why such a drying process is applied to the shell-sheet S to adjust the moisture content is because mutual adhesiveness (joint property) of the sheets in a later stage of joining is enhanced. Furthermore, in Embodiment shown in FIG. 1, in the dryer main body 15R formed above the casting drum 22, a medium wavelength infrared ray is applied to the two surfaces of the shell-sheet S to dry the shell-sheet S (this is double-sided drying). Note that, the surface which is not in direct contact with the casting drum 22 is first dried (this is referred to as a front-surface drying for convenience sake) and thereafter, the surface in direct contact with the casting drum 22 is dried (this is referred to as back surface drying for convenience sake). Note that, looking front surface drying/back surface drying from another standpoint, drying the surface corresponding to the outer side of the soft capsule 1 finally obtained is front surface drying, whereas drying the surface corresponding to the inside of the capsule, i.e., the surface in direct contact with the filling N is back surface drying.

Furthermore, in the Embodiment, the shell-sheet S is removed from the casting drum 22 and dried separately while it is transported by feed roles 23. The transport path used herein is designated by reference numeral 24. More specifically, the transport paths 24 for front surface drying and back surface drying are formed by inverting the front and back surfaces of the shell-sheet S by the feed roles 23, a medium wavelength infrared ray is applied to the sheet (front/back) from the above while keeping a predetermined distance. For this, in each of the transport paths 24, a medium wavelength infrared heater 25 for emitting a medium wavelength infrared ray is provided. Furthermore, below the heater, a reflecting plate 26 is provided with the shell-sheet S interposed between them in order to dry a non-irradiation surface to some extent with the intention to improve heat efficiency.

Note that, four medium wavelength infrared heaters 25 are provided for each of the front surface and back surface; however, it is not necessary to use all of them, and a requisite number of heaters may be used depending upon e.g., the original blending ratio of the shell material 2A and the desired moisture content value to be obtained by drying to apply an appropriate amount of energy to the shell-sheet S.

Furthermore, the shell-sheet S is heated simultaneously with drying by medium wavelength infrared irradiation and thus the shell-sheet S tends to be deformed by heat during drying (heater temperature is, e.g., about 900° C.). More specifically, since shell-sheet S is transported, tensile force is always applied to the shell-sheet S in a feed direction (transport direction). Therefore, the shell-sheet S is easily deformed by heating so as to extend in the feed direction (longitudinal direction) and easily shrinks in the width direction (depth direction) in perpendicular to this. The extension in the longitudinal direction likely appears as slack due to the self-weight of the shell-sheet S. To prevent the slack, a support 27 such as a roller etc. is provided underneath the shell-sheet S.

Note that, in the figure, reference symbols (trailing reference symbols) "A" and "B" added to e.g., the transport path 24 and the medium wavelength infrared heater 25 mean the surfaces upon which they function. More specifically, to the member which functions upon the front surface of the shell-sheet S, reference symbol "A" is added, whereas to the member which functions upon the back surface, reference symbol "B" is added.

Furthermore, to prevent excessive heating of the shell-sheet S during drying, air is supplied along the surface of the shell-sheet S (i.e., irradiation surface with a medium wavelength infrared ray). The air is supplied in the same direction as the sheet feed direction, i.e., supplied from the upstream side to the downstream side of the feed direction. By virtue of this, the shell-sheet S is appropriately cooled, and air flow in the transport path 24 becomes stable (a kind of rectification), and a deformation such as slack can be prevented.

Note that, in Embodiment, an air spray member 28 provided on the upstream side is a slit nozzle type member having a long thin slit along the width direction of the shell-sheet S and formed so as to spray air uniformly from the opening along a sheet surface. On the other hand, an air suction member 29, which is provided on the downstream side, has a larger opening portion than that of the air spray member 28 so as to suction air by a large area.

Furthermore, as mentioned above, since the temperatures of the transport path 24 and the shell-sheet S tend to increase during drying, a thermometer 30 is provided below the medium wavelength infrared heater 25 (immediately under the shell-sheet S) so as to control temperature.

Note that, since an operator who operates the filling machine 10 or monitors operation of the filling machine 10 preferably avoids straightly looking light (a medium wavelength infrared ray) emitted from the medium wavelength infrared heater 25, a vertically movable cover 31 is preferably provided to a side surface portion of the dryer 15, for example, as shown in the enlarged view of FIG. 1, to actively interrupt irradiation light from the medium wavelength infrared heater 25. Note that, in moving the cover 31 up and down, two vertical slits 32 are formed in the cover 31 in advance, as also shown in FIG. 1. At the same time, a wing bolt 33 is attached to an apparatus frame (dryer main body 15A) through the slit 32 so as to move the cover 31 up and down or fix it by fastening (screwing)/releasing (unscrewing) the wing bolt 33.

Figure 3:
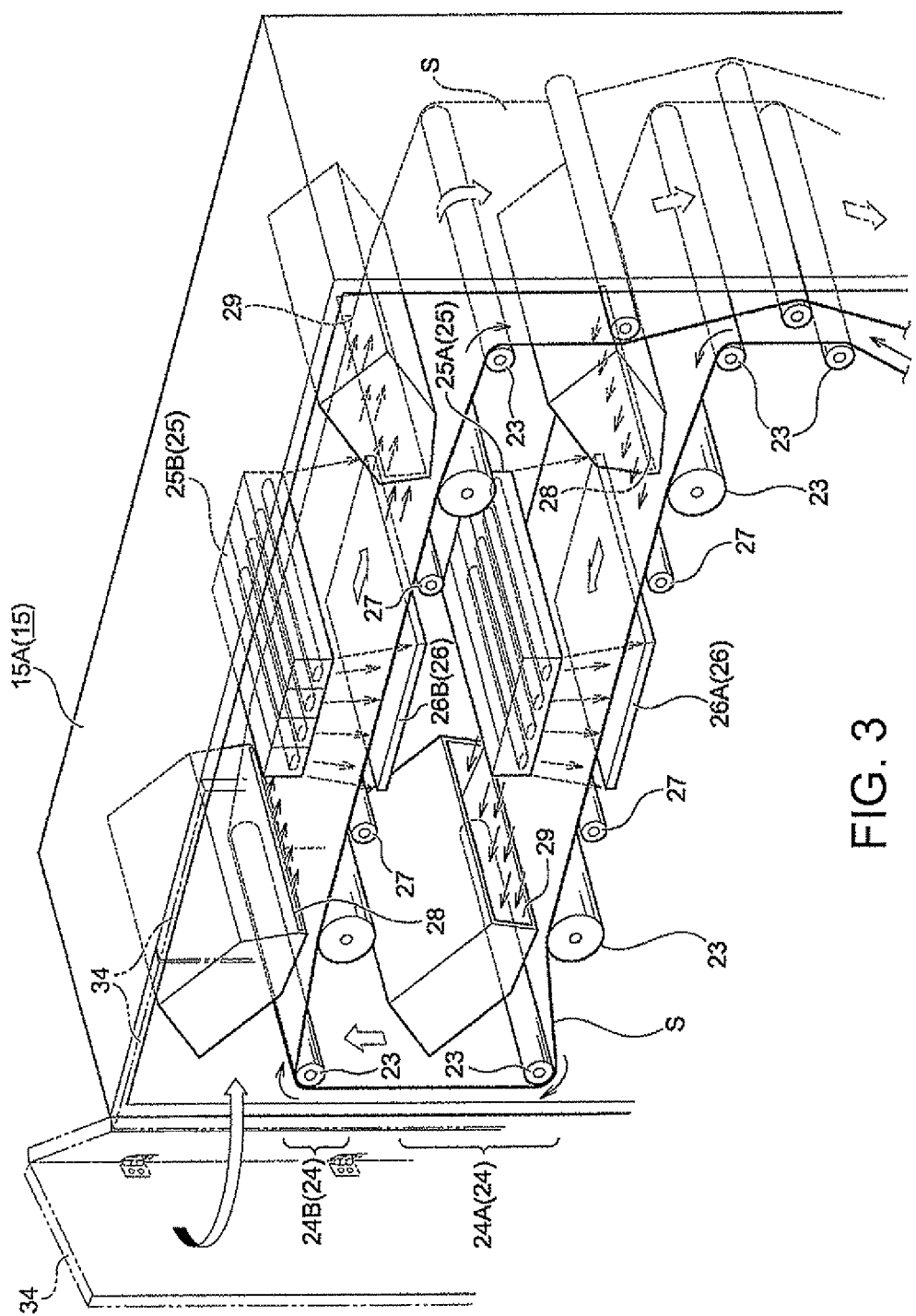
FIG. 3 is an enlarged perspective view of the dryer having a medium wavelength infrared irradiation mechanism.

Furthermore, also at the site where the transport path 24 is inverted, that is, where the air spray member 28 and the air suction member 29 are provided, a cover 34, for example, as shown in FIG. 3 is preferably provided. This is because the space of a dryer main body 15A is separated from the external space (manufacturing room) to make a compartment, by the covers 31 and 34. More specifically, by separating the inner space of the dryer main body 15A by the covers 31 and 34, air is more accurately supplied along the sheet surface from the air spray member 28 to the air suction member 29 (it is possible to prevent airflow from dispersing) and deposition of e.g., dust on the shell-sheet S during drying can be prevented. Note that, the cover 34 shown in FIG. 3 is formed of a transparent material through which an operator can observe what is going on inside during manufacturing and formed so as to compactly fold (fold in the middle) and rotatory and horizontally move.

The site mentioned in the foregoing is the sheet molding section 11. Thereafter the shell-sheet S is supplied to a site in which the capsule molding section 12 is provided. A feed role 37 is provided so as to relay both molding sections. More specifically, the shell-sheet S whose moisture content is appropriately controlled by the sheet molding section 11 (dryer 15) is fed through a plurality of feed roles 37 in a zigzag fashion to the capsule molding section 12.

Figure 5:
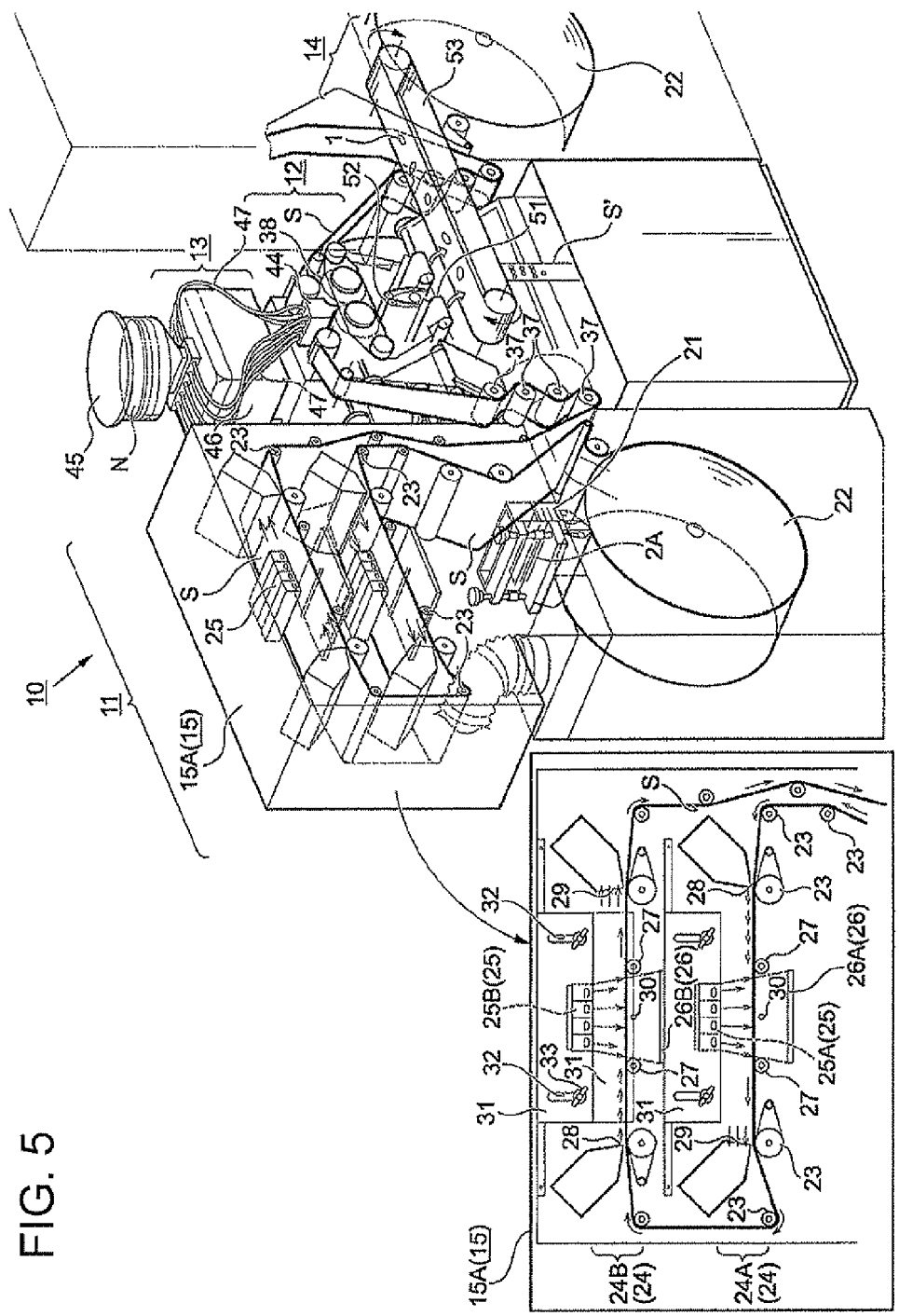
FIG. 5 is a plan view of a pair of die rolls.

Next, the capsule molding section 12 will be described. This section is constituted of a pair of die rolls 38 (right and left rolls) as a main member, for example, as shown in FIGS. 4 and 5. Of the die rolls 38, one is fixed, and the other is constructed to freely move back and forth toward the fixed die roll 38.

Each of the die rolls 38 has molding recesses 39 having an appropriate shape in the surface and molding projections 40 in the periphery of the recesses. For example, when the soft capsule 1 having a virtually spindle or virtually spheroidal shape is molded, the molding recesses 39 each can be formed into an oval with the center depressed. However, in this Embodiment where starch is used as a main component, the molded soft capsule 1 shrinks more significantly than the capsule using gelatin as a main component. Therefore, taking the shrinkage into consideration in advance, the molding recesses 39 are formed. The pair of die rolls 38 are rotatory moved such that the molding projections 40 are allowed to correspond to each other. In this way, the shell-sheets S supplied so as to face each other between the die rolls 38 are led in and butted in a timely manner, and the peripheral portions of the capsule are stitched (joined).

Note that, in the Embodiment, a liquid-form filling is intended to be used as the filling N contained in (coated with) the shell portion 2. When the filling N is fed toward the shell-sheet S by applying spray pressure (liquid pressure), it can be expected that the shell-sheet S is deformed so as to follow the shape of the molding recess 39. Accordingly, without taking any active measure, a pocket P for receiving the filling N is naturally formed in the shell-sheet S in time for supply (feed) of the filling N.

Of course, the pocket P can be actively formed in the shell-sheet S before the filling N is supplied. This is a suction hole 41, as shown, for example, in FIGS. 4 and 5. More specifically, in this case, the shell-sheet S fed between the die rolls 38 is actively suctioned through the suction hole 41 formed in the bottom of each molding recess 39 to form the pocket P (curved) for receiving liquid inclusion N in advance. Note that, as another mode for actively forming the pocket P, for example, emboss processing can be mentioned, which is applied to the shell-sheet S in a stage before the filling N is supplied, to form the pocket P. Note that as to a mechanism for forming the pocket P by sucking the shell-sheet S, the present applicant already filed a Patent Application and was granted a patent (Japanese Patent Laid-Open No. 10-211257 (Japanese Patent No. 3211148) "Gelatin capsule including a particulate matter, and manufacturing method and apparatus therefor").

Next, the filling supply section 13 will be described. This is a section for supplying the filling N such as a liquid-state filling to the shell-sheets S in time for joining of the shell-sheets S, more specifically, before the periphery of the capsule is completely stitched. This section is constituted of a protruding segment 44 formed such that a tip thereof fully enters between the die rolls 38, as a main member.

In the filling supply section 13, a raw-material liquid hopper 45 is provided in the upper portion, for example, as shown in FIG. 1, for storing a raw-material liquid (filling N). Below the raw-material liquid hopper 45, a pump unit 46 is provided. This is appropriately formed by combining a plurality of plungers, etc. The filling N is sprayed through a plurality of passages e.g., with a predetermined timing and pressure, passes through a delivery pipe 47 and ejected from the segment 44 to the shell-sheet S.

Next, a capsule take-out section 14 provided below the die rolls 38, for taking out the molded soft capsule 1 will be described. The molded soft capsule 1 is often fitted in the molding recess 39 of the die roll 38, for example, as shown in FIG. 4. Such a soft capsule 1 is taken out by scraping it off by a scraping brush 50 provided in contact with the die roll 38, while transporting the soft capsule 1 scraped off by a pair of forward conveyers 51, which are provided along a rotation shaft of the die roll 38, toward the front surface of the filling machine 10 (see FIG. 1). Furthermore, between the pair of forward conveyers 51, a free roller 52 (the width can be freely controlled) is provided, for example, as shown in FIG. 1, for sandwiching a blank sheet S', from which the soft capsule 1 has been punched out, by both sides, and feeding it downward as it is. Note that, in consideration of the case where the soft capsule 1 remains also in the blank sheet S', the free roller 52 is preferably constituted such that the soft capsule 1 remaining in the blank sheet S' can be discharged on either one of the forward conveyers 51. Furthermore, the soft capsule 1 is transported by the forward conveyer 51 to the front surface of the filling machine 10 and thereafter, further transferred to another conveyer 53, and transported to the next drying step.

Note that in the capsule molding section 12, two shell-sheets S, are fed so as to face each other between the pair of die rolls 38, for example, as shown in FIG. 4, and the filling N is supplied from the segment 44 positioned in the above with a predetermined timing. To describe more specifically, two shell-sheets S are supplied between the die rolls 38 and formed into individual capsules by stitching the periphery thereof (the periphery of the molding recess 39) with the help of butt joint function of a number of molding projections 40 provided in the peripheral surface thereof. At this time, since a pressure of, for example, about 150 to 200 kg, is applied to the shell-sheet S by the molding projections 40, the suture portion is effectively gelatinized and stitched.

After completion of stitching of the peripheral portion, the soft capsule 1 is taken out from e.g., the molding recess 39 and the blank sheet S' as described above and then dried. Note that, in the drying process, a tumbler dryer (rotatory drum type dryer) is generally used in accordance with the shape and properties of the soft capsule 1.

[Manufacturing Method]

The soft capsule manufacturing apparatus 10 of the present invention (filling machine 10) has the aforementioned basic structure. A mode for manufacturing the soft capsule 1 by the filling machine 10 will be described below; at the same time, the method of manufacturing a soft capsule according to the present invention will be described.

First, a mode for mixing components (shell material 2A) constituting the shell portion of the soft capsule 1 and supplying the components to the filling machine 10 will be described.

Generally, in mixing and supplying the shell material 2A of the soft capsule 1 to the filling machine 10, there are a process using a bucket type heat dissolution pot and a process for continuous supplying them by an extruder. Both processes can be used also in the present invention; however, the process using a bucket type heat dissolution pot will be described herein.

For example, when the non-animal derived soft capsule 1 is manufactured, in the heat dissolution step for melting the shell material 2A, starch, λ carrageenan, a metal salt, dextrin, a plasticizer, and water are placed in a heat dissolution pot and dissolved by heating at a temperature of 90 to 120° C. (usually 110° C.), for 60 to 100 minutes (usually 80 minutes) while stirring by a stirrer at a pressure of 0.05 to 0.3 MPa (usually 0.2 MPa) and a rotation rate of 50 to 70 rpm.

Next, a defoaming step consisting of two stages is performed. The first-stage defoaming step is performed at a defoaming temperature of 100 to 110° C. (usually 105° C.) at a defoaming pressure of −400 to −600 mmHg (usually −500 mmHg) in terms of gauge pressure regarding an atmospheric pressure as 0 for a defoaming time period of 15 to 70 minutes (usually 30 minutes). At this time, the stirrer is rotated at a rotation rate of 10 rpm for initial 5 to 15 minutes (usually 10 minutes) and thereafter, defoaming is performed with the stirrer stopped.

The second-stage defoaming step is performed at a defoaming temperature which is increased to 110 to 130° C. (usually 120° C.) at a defoaming pressure of −400 to −600 mmHg (usually −500 mmHg) in terms of gauge pressure regarding an atmospheric pressure as 0 for a defoaming time period of 10 to 20 minutes (usually 15 minutes).

The vacuum dissolution pot herein for use in the heat dissolution step and the defoaming step is not particularly limited; however, for example, a high-viscosity vacuum stirrer, Type: SY-HMD-20 (trade name, manufactured by SHANG YUH MACHINE, CO., LTD) can be used.

Furthermore, as a vacuum pump used in the defoaming step is not particularly limited and, for example, a water seal vacuum pump (Type: LEH100Ms, manufactured by Kashiyama Industries, Ltd.) can be used.

Note that, after the defoaming, the resultant solution-state shell material 2A is preferably transferred to a pressure-proof subdivision tank and stored while heating at 60 to 90° C. (usually 75° C.) for about 12 to 24 hours.

In the step of supplying the solution-state shell material 2A thus obtained to the filling machine 10, the shell material 2A is extruded from the subdivision tank at a pressure of 0.01 to 0.1 MPa (usually 0.05 MPa) and stored in the spreader box 21 of the filling machine 10. Furthermore, by controlling the interval between the casting drum 22 and the spreader box 21, the shell-sheet S having a predetermined thickness is prepared. Note that, the temperature of the casting drum 22 herein is kept at a predetermined temperature of 17 to 22° C. (usually the temperature is 20° C.) by air cooling or water cooling.

Furthermore, it is preferable that the humidity of the filling chamber (humidity of the manufacturing room) is maintained at a predetermined humidity of 20 to 26% RH (usually 23% RH) and the temperature of the filling chamber (temperature of the manufacturing room) is maintained at a predetermined temperature of 22 to 27° C. (usually 25° C.)

Next, a mode for drying the shell-sheet S thus obtained by the dryer 15 having a medium wavelength infrared irradiation mechanism will be described.

The shell-sheet S ejected from the spreader box 21 is mounted on the casting drum 22 and rotated by about a ¾circle (about 270 degrees). Thereafter, the shell-sheet S is removed from the casting drum 22 and sent to the transport path 24 formed e.g., in the above, in which two surfaces are dried by medium wavelength infrared irradiation. To explain more specifically, the shell-sheet S fed from the casting drum 22 first passes through a transport path 24A, in which the front surface (outside a capsule) is dried by a medium wavelength infrared heater 25A and thereafter, inverted by the feed roles 23 and sent to the next transport path 24B, in which, in turn, the back surface (inside a capsule) is dried by a medium wavelength infrared heater 25B. In this manner, both surfaces of the shell-sheet S are dried.

In drying the shell-sheet S of the present invention, drying is performed such that the moisture content of the shell-sheet S is reduced by medium wavelength infrared ray energy emitted from the medium wavelength infrared heater 25 to preferably 19 to 29%, more preferably 21 to 27%, and particularly preferably 23 to 25% (the moisture content is measured by MOISTURE BALANCE (trade name), Type: MOC-120H manufactured by Shimadzu Corporation). This is because if the moisture content of the shell-sheet S is 19% or less or 29% or more, adhesiveness between the shell-sheets S tends to unfavorably decrease.

The wavelength of the medium wavelength infrared ray emitted from the medium wavelength infrared heater 25 is preferably 0.8 to 4.0 µm, more preferably 1.3 to 3.0 µm, and particularly preferably 2.5 to 2.7. As the medium wavelength infrared heater 25 herein, any medium wavelength infrared heater can be used as long as it emits a wavelength of the medium wavelength infrared ray satisfying the above conditions and it is commercially available. For example, a medium wavelength infrared heater, Type: MBS1600/250 (trade name) manufactured by Heraeus K.K. can be applied.

Note that, in the present invention, since what is applied to the shell-sheet S is medium wavelength infrared ray, heat permeates into the interior of the sheet, with the result that the moisture content in the thickness direction of the sheet can be equalized. By virtue of this, after irradiation, joining can be extremely satisfactorily performed by the die rolls 38. In this respect, a prominent effect can be produced.

Note that, if the shell-sheet S is dried simply by applying hot air thereto, only the surface of the shell-sheet S is dried. Accordingly, the interior of the sheet and the surface thereof become different in moisture content. As a result, the following joint cannot be often satisfactorily performed. This occurs significantly when starch is used as a main component.

Furthermore, in the Embodiment, reflecting plate 26A/26 B are provided below the medium wavelength infrared heaters 25A/25B. Therefore, the shell-sheet S passes through the space between the medium wavelength infrared heater 25 and the reflecting plate 26 during drying, thereby improving heat efficiency.

Furthermore, the shell-sheet S tends to be deformed with heat from the heater during drying. However, in the Embodiment, slack due to heat can be prevented by the presence of the support 27 such as a roller etc.

Furthermore, air is supplied to the irradiation surface of the shell-sheet S in the same direction as in the feed direction of the sheet. Therefore, an excessive temperature increase of the sheet can be prevented.

The shell-sheets S thus dried and appropriately controlled in moisture content are then fed to the capsule molding section 12 (between the die rolls 38) via the feed roles 37 and joined in the section 12. Furthermore, the filling N is supplied to the shell-sheets S to be joined in time for joining to form the soft capsule 1 containing the filling N in the shell portion 2. The soft capsule 1 thus formed is fit in the molding recess 39 of the die rolls 38 and remains in the blank sheet S' as mentioned above. The capsule is then taken out from these and dried.

Note that, a capsule fill rate is usually expressed by a rotation rate (rpm: revolution per minute) of the die roll 38 (mold). In manufacturing the non-animal derived soft capsule 1 using starch, λ carrageenan, a metal salt, dextrin, a plasticizer, and water, the moisture content of the shell-sheet S can be controlled by the dryer 15 having the medium wavelength infrared irradiation mechanism even if the rotation rate of the die roll 38 (mold) is increased. Therefore, productivity can be enhanced by increasing the rotation rate of the die roll 38 (mold).

Other Embodiments

A basic technical idea of the present invention is described in the aforementioned embodiment and the following modification is further conceivable. In the embodiment previously mentioned, the transport paths 24A and 24B in which a treatment is applied to the front surface and back surface of the shell-sheet S, respectively, are separately formed and a medium wavelength infrared ray is applied by the medium wavelength infrared ray heaters 25A and 25B to dry both surfaces of the shell-sheet S. However, in the case where the shell-sheet S can be sufficiently dried up to the interior thereof by single-sided irradiation, the sheet may be dried in either one of the transport paths 24A/24B.

Naturally, in such a case where the shell-sheet S can be uniformly dried up to the interior thereof by single-sided irradiation, the transport path 24 is not necessarily formed upside down. The transport path 24 for drying (irradiation) is formed between the site at which the shell-sheet S is removed from the casting drum 22 and the site at which the shell-sheet S is fed to the joint (between the pair of die rolls 38), the sheet can be dried by applying a medium wavelength infrared ray in the transport path 24.

Furthermore, in the case where the shell-sheet S can be dried by single-sided drying, drying can be performed without particularly providing the transport path 24. When drying is performed in this manner, for example, as shown in FIG. 6, the medium wavelength infrared heater 25 is provided in the proximity of the casting drum 22 (at the site where the sheet is ejected from the spreader box 11 and then rotated by about a ¼ circle (about 90 degrees)) and the shell-sheet S mounted on the casting drum 22 (before the sheet S is removed from the casting drum 22) is dried.

Figure 6:
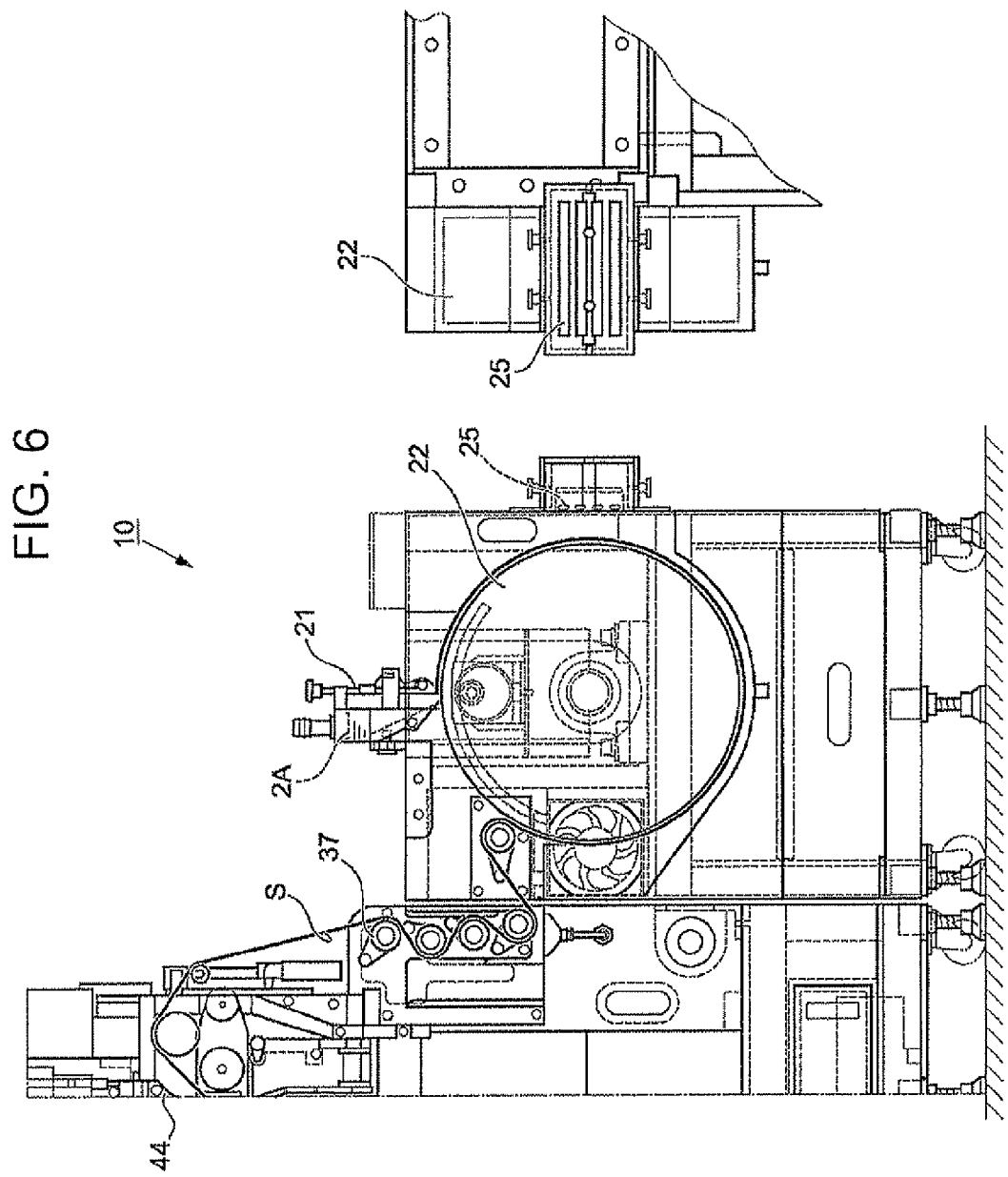
FIG. 6 is a front view of the filling machine having the dryer having a medium wavelength infrared irradiation mechanism provided at a side of a casting drum (without particularly providing a transport path) for drying a shell-sheet (showing single-sided drying), together with a side view of the dryer as viewed from the right side thereof.

Note that, it is considered that the filling machine 10 shown in FIG. 6 above is preferable for manufacturing the conventional soft capsule 1 containing gelatin as a main component. This is because a sheet containing gelatin as a main component is conceivably dried by a means having drying capacity less than the medium wavelength infrared ray. In this case, if the medium wavelength infrared heater 25 is not functioned, the heater 25 not having the transport path 24 can be in a conventional drying mode, more specifically, in a mode for drying only one of the surfaces (outer surface of a capsule) of the capsule shell-sheet S by the casting drum 22 alone (moisture content: 19 to 23%).

Note that, single-sided drying on the casting drum 22 appears to be the same as that performed by the conventional rotary die system automatic soft capsule manufacturing machine; however, in the present invention, drying is performed by irradiation of a medium wavelength infrared ray and not by merely blasting. Therefore, the non-animal derived shell-sheet S containing starch, carrageenan, a metal salt, dextrin, a plasticizer, and water can be sufficiently dried and the adhesiveness of the shell-sheet S can be enhanced. In addition, both surfaces of the shell-sheet S can be freely dried.

On the other hand, as to such single-sided drying, a case where an initial moisture content is high and a case of requiring a further higher drying capacity are conceivable. Such cases, the transport paths 24A and 24B (shown in FIG. 1 above) are further formed in the filling machine 10 shown in FIG. 6 above. In this way, not only drying applied to the sheet mounted on the casting drum 22 (single-sided drying) but also drying applied to the sheet taken out in the transport path 24 (double-sided drying) can be performed.

Figure 7:
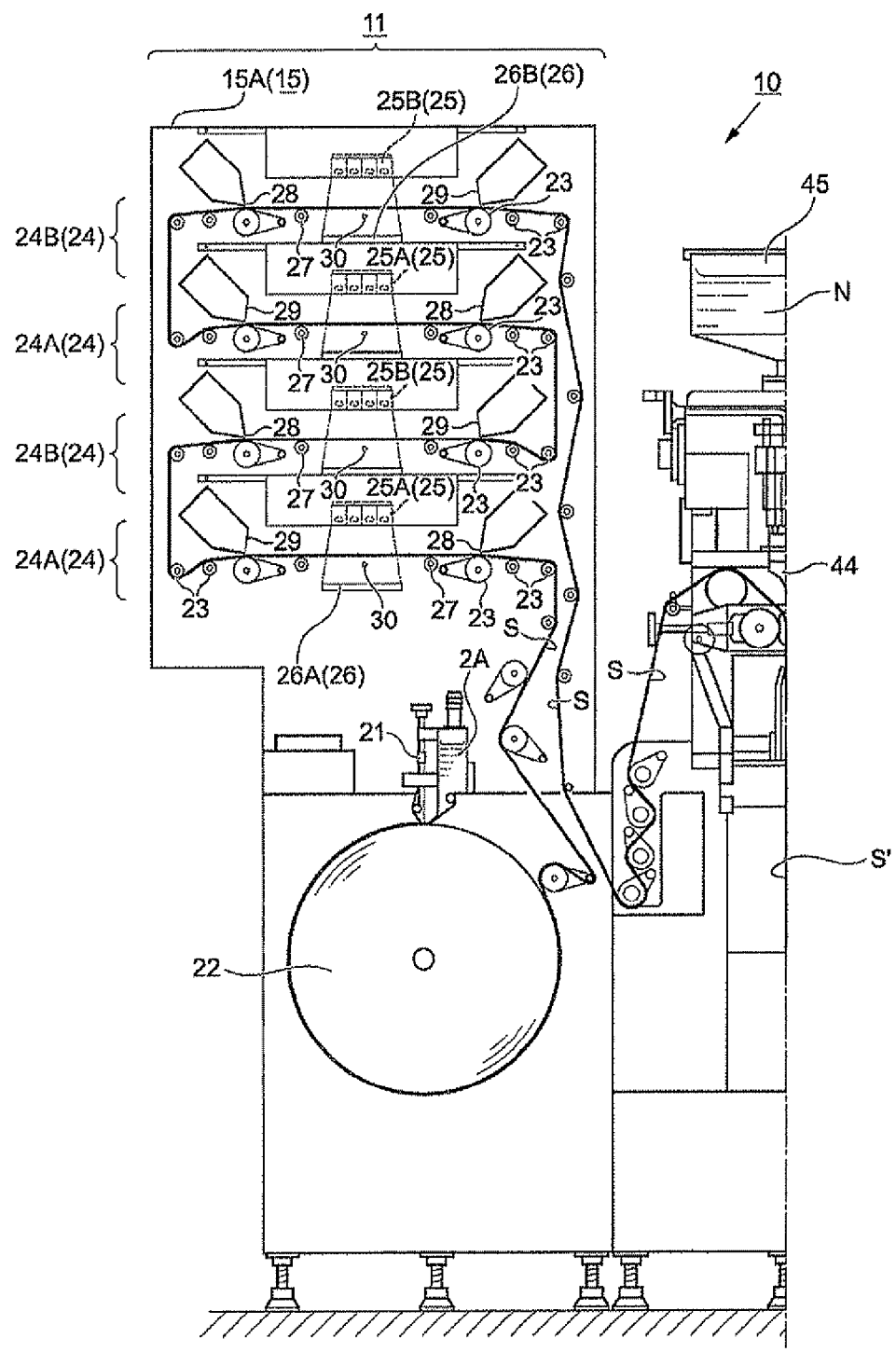
FIG. 7 is a front view of the filling machine having four-stage transport path for drying with medium wavelength infrared irradiation such that the front surface and back surface of a shell-sheet each can be dried (irradiated) twice (showing double-sided drying)

Furthermore, in the case where a further higher drying capacity is required, for example, as shown in FIG. 7, if the transport path 24 for use in double-sided drying is formed in three stages or more, for example, drying of the front surface and the back surface can be performed twice for each.

Even if the medium wavelength infrared heater 25 is provided in multi stages of three stages or more, of course, it is not necessary to turn on the medium wavelength infrared heaters 25 provided in all the stages. It is a matter of course that some of the heaters can be turned on as needed, depending upon an initial component of the shell material 2A and the desired moisture content to be controlled by drying.

Figure 2:
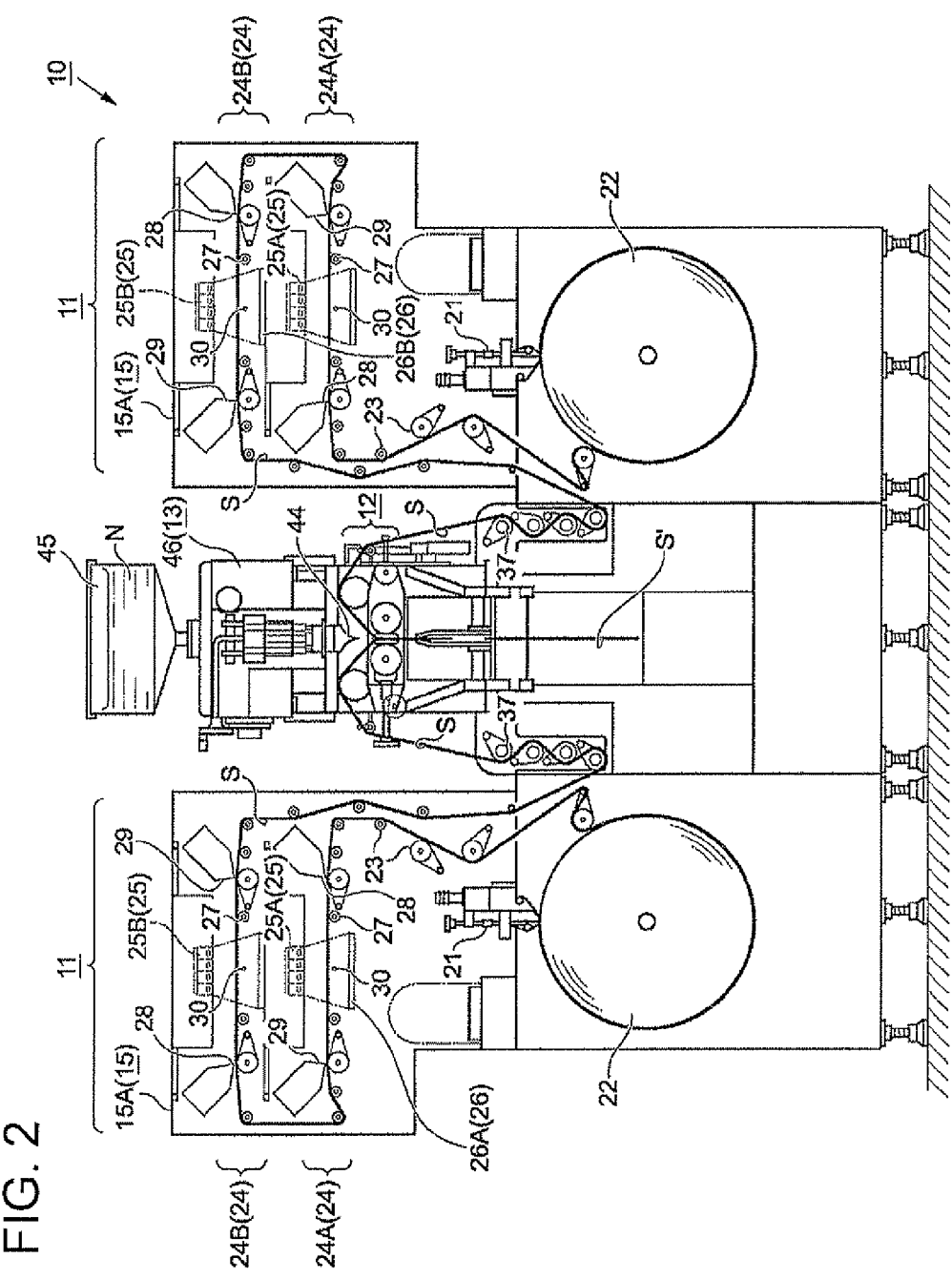
FIG. 2 is a front view of the manufacturing apparatus (filling machine) of the present invention.
Figure 8:
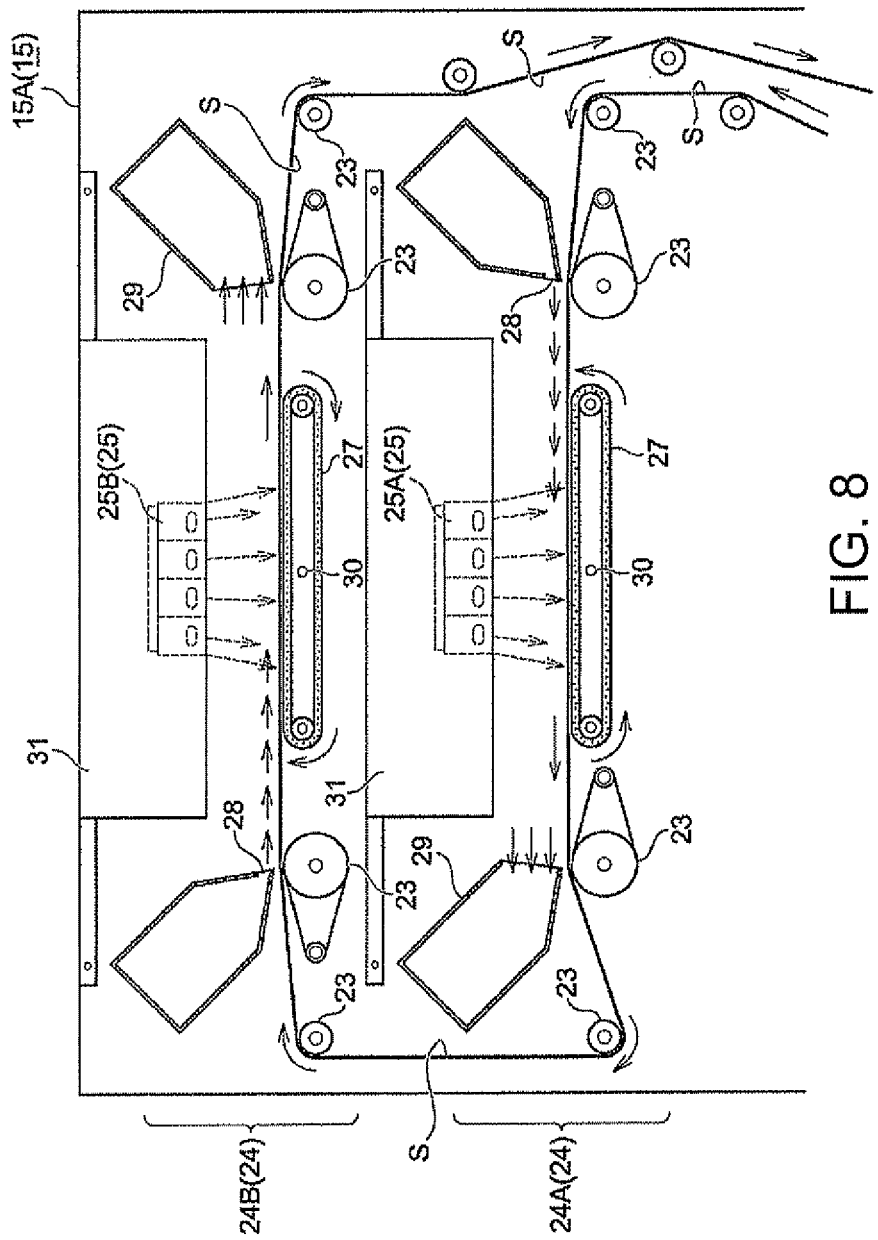
FIG. 8 is a front view showing an embodiment in which a shell-sheet under drying is supported from below by a conveyer.

Furthermore, the aforementioned Embodiments of FIG. 1 to FIG. 3, as the support 27 for supporting the shell-sheet S irradiated with a medium wavelength infrared ray from below, a roller is used; however, the support 27 is not always limited to the roller and, for example, a conveyer and the like can be used, as shown in FIG. 8. Note that, the conveyer used herein is driven at the same transport rate as that of the shell-sheet S.

Next, the present invention will be further specifically described with reference to more specific Examples; however, the present invention is not limited to these Examples, and can be applied to all substances that can be encapsulated, such as an animal oil and a vegetable oil, a mixture of an animal oil and a vegetable oil, and further a mixture of fat and oil with any one of fat and oil such as suspension oils containing an animal/vegetable extract and a powdery extract.

Note that, prior to description of Comparative Examples and Examples, the evaluation items and the evaluation method used in Comparative Examples and Examples will be described.

(1) Adhesiveness Evaluation
  Evaluation was visually made by a microspore as follows.
  ⊚: extremely satisfactory adhesion
  ○: Good adhesion
  Δ: Poor adhesion
  X: No adhesion
(2) Liquid Spill Evaluation
  1000 capsules were allowed to stand still for 12 hours, the number of capsules of "liquid spill", i.e., leakage of a filling, were counted. A liquid spill rate was computationally obtained by percentage.
(3) Defoaming Defect Evaluation
  The number of defoaming-defective capsules having visually observable foams in the shell-sheet S was counted per 1000 capsules. In this manner, a percent defoaming-defective was computationally obtained by percentage.

Comparative Example 1, Comparative Example 2, Comparative Example 3

The capsule shell components shown in Table 1 are placed in a heat dissolution pot and dissolved under a pressure of 0.2 MPa by heating at a temperature of 110° C. for 80 minutes while stirring by a stirrer at a rotation rate of 50 to 70 rpm.

Next, a defoaming step consisting of two stages is performed. The first-stage defoaming step is performed at a defoaming temperature of 105° C. at a defoaming pressure of −500 mmHg in terms of gauge pressure regarding an atmospheric pressure as 0 for a defoaming time period of 30 minutes. At this time, the stirrer is rotated at a rotation rate of 10 rpm for initial 10 minutes and thereafter, defoaming is performed with the stirrer stopped. The second-stage defoaming step is performed at a defoaming temperature which is increased to 120° C. at a defoaming pressure of −500 mmHg in terms of gauge pressure regarding an atmospheric pressure as 0, for a defoaming time period of 15 minutes.

After defoaming, the resultant soft-capsule shell solution was transferred to a subdivision tank and stored at 75° C. for about 15 hours, and then put in use.

As the filling machine, a conventional rotary die system automatic soft capsule manufacturing machine was used. The resultant soft-capsule shell solution was ejected from the spreader box and extended on the casting drum placed both sides of the filling machine to obtain a sheet-form (shell-sheet). The shell-sheet was guided into the filling machine. Immediately after the filling (a mixture of MCT (70 weight %) and lecithin (30 wt %)) was supplied and pressed by a mold (die roll) to obtain soft capsules.

<Filling Conditions>
  Temperature of casting drum: 20° C.
  Temperature of segment section: 45° C.
  Rotation rate of die roll: 1.5 rpm in Comparative Examples 1 and 2,
  3.0 rpm in Comparative Example 3
  Humidity of filling chamber: 23% RH
  Temperature of filling chamber: 25° C.

Example 1

The capsule shell components shown in Table 1 are placed in a heat dissolution pot and dissolved under a pressure of 0.2 MPa by heating at a temperature of 110° C. for 80 minutes while stirring by a stirrer at a rotation rate of 50 to 70 rpm.

Next, a defoaming step consisting of two stages is performed. The first-stage defoaming step is performed at a defoaming temperature of 105° C. at a defoaming pressure of −500 mmHg in terms of gauge pressure regarding an atmospheric pressure as 0 for a defoaming time period of 30 minutes. At this time, the stirrer is rotated at a rotation rate of 10 rpm for initial 10 minutes and thereafter, defoaming is performed with the stirrer stopped. The second-stage defoaming step is performed at a defoaming temperature which is increased to 120° C. at a defoaming pressure of −500 mmHg in terms of gauge pressure regarding an atmospheric pressure as 0, for a defoaming time period of 15 minutes.

After defoaming, the resultant soft-capsule shell solution (shell material 2A) was transferred to a subdivision tank and stored at 75° C. for about 15 hours, and then put in use.

As the filling machine 10, a soft capsule manufacturing machine equipped with the dryer 15 having a medium wavelength infrared irradiation mechanism of the present invention was used.

The resultant solution-state shell material 2A was extended on the casting drum 22 placed both sides of the filling machine 10 to obtain a sheet-form (shell-sheet S). The shell-sheet S was guided into the filling machine 10, while drying the shell-sheet S by the medium wavelength infrared heater 25 such that the moisture content of the sheet became 24%. Immediately after the filling (a mixture of MCT (70 weight %) and lecithin (30 wt %)) was supplied and pressed by a mold (die roll 38) to obtain the soft capsules 1.

<Filling Conditions>

Temperature of casting drum: 20° C.

Medium wavelength infrared heater (Type: MES1600/250 manufactured by Heraeus K.K.): wavelength 2.6 μm Temperature of segment section: 45° C.

Rotation rate of die roll: 3.0 rpm

Humidity of filling chamber: 23% RH

Temperature of filling chamber: 25° C.

TABLE 1

|  |  | Comparative Example 1 | Comparative Example 2 | Comparative Example 3 | Example 1 |
|---|---|---|---|---|---|
| Composition of capsule coating | Starch (parts by weight) |  | 100 |  | 100 |
|  | Dextrin (parts by weight) |  | 10 |  | 10 |
|  | λ carrageenan (parts by weight) |  | 10 |  | 10 |
|  | Glycerin (parts by weight) |  | 50 |  | 50 |
|  | Water (parts by weight) | 80 | 110 | 110 | 110 |
|  | Sodium dihydrogen phosphate (parts by weight) |  | 2 |  | 2 |
|  | Potassium chloride (parts by weight) |  | 0.1 |  | 0.1 |
| Filling conditions | Type of filling machine | Conventional rotary die system automatic soft capsule manufacturing machine | | | Soft capsule manufacturing machine equipped with dryer having medium wavelength infrared irradiation mechanism |
|  | Die roll rotation rate (rpm) | 1.5 | 1.5 | 3 | 3 |
| Evaluation | Adhesiveness | Δ | Δ | X | ⊚ |
|  | Liquid-spill rate of capsule filling (%) | 1.8 | 3.5 | 47.3 | 0.0 |
|  | Percent defoaming defective (%) | 35.6 | 1.2 | 2.1 | 0.2 |

As described in Comparative Example 1, in the case of the conventional rotary die system automatic soft capsule manufacturing machine (die roll rotation rate: 1.5 rpm), if the moisture content of a capsule shell material was 80 parts by weight, air incorporated in the shell solution was hardly removed. As a result, a defoaming-defective capsule rate increased.

On the other hand, as shown in Comparative Example 2, in the case of the conventional rotary die system automatic soft capsule manufacturing machine (die roll rotation rate: 1.5 rpm), if the moisture content of a capsule shell material was 110 parts by weight, defoaming property was improved compared to Comparative Example 1 and thus a percent defoaming-defective was low; however, adhesiveness of a capsule was low. As a result, there were some capsules causing leakage of a capsule filling (a mixture of MCT (70 weight %) and lecithin (30 wt %)).

As described in Comparative Example 3, when capsules were formed by the conventional rotary die system automatic soft capsule manufacturing machine from the same capsule shell material as in Comparative Example 2, having a moisture content of 110 parts by weight at a die roll rotation rate of 3.0 rpm which was increased from 1.5 rpm, a capsule adhesion surface was not sufficiently adhered. As a result, immediately after capsule formation, leakage of a capsule filling (a mixture of MCT (70 weight %) and lecithin (30 wt %)) occurred and a liquid spill rate was high.

As described in Example 1, when the soft capsule manufacturing apparatus (filling machine) 10 of the present invention was used, even if the die roll rotation rate was increased twice (1.5→3.0 rpm) as high as those Comparative Examples 1, 2, and 3, the soft capsule 1 having a low percent defoaming-defective, an extremely satisfactory adhesiveness, and no liquid spill, was able to be manufactured.

In manufacturing the soft capsule 1 herein, difficulty thereof when the shell material 2A containing starch as a main component (difficulty compared to the shell material containing gelatin as a main component) will be described. When starch is contained as a main component, it is necessary to improve the drying capacity of the filling machine 10 as mentioned above; however, to attain this, it is not sufficient if the long transport path 24 for drying is just simply formed to thereby perform drying for a long time. This is because deformation due to heat occurs by drying. Particularly when the length of the transport path 24 is extended, tension (tensile force) applied by transporting is increased by the extension (the longer the transport path, the larger the tension is applied). Consequently, the complete-form soft capsule 1 is easily deformed. Specifically, the size of the molding recess 39 of the die roll 38 is considered substantially the same as the complete-form soft capsule 1 (in the case where gelatin is a main component, the complete-form soft capsule 1 has the same size as that of the molding recess 39). In contrast, the soft capsule 1 formed of starch as a main component, greatly shrinks in the rotation direction of the die roll 38 compared to the actual size of the molding recess 39 (feed direction of the shell-sheet S) (for example, as indicated by a two-dot chain line in an enlarged view of FIG. 5, the soft capsule shrinks by about 10% to 30%, and thus it is extremely difficult to manufacture a soft capsule containing starch compared to that containing gelatin as a main component.

INDUSTRIAL APPLICABILITY

The present invention can be used in the fields of "medical products", "specially designated health foods", "so-called health foods", and foods. Other than these, if another type of filling, for example, an industrial preparation, is selected, the present invention can be used in the industrial field.

The invention claimed is:

1. A method for manufacturing a soft capsule containing a filling within a shell portion formed of a shell-sheet, comprising ejecting a molten shell material in the form of a sheet having an almost uniform thickness from a spreader box, and cooling the shell-sheet ejected from the spreader box by a casting drum, and supplying shell-sheets thus obtained between a pair of die rolls so as to face each other, joining the shell-sheets by butt joint function of the die rolls, and supplying the filling from a segment in a filling supply section between the shell-sheets in time for joining, wherein the shell portion is formed by blending starch, λ carrageenan, a metal salt, dextrin, a plasticizer, and water as components for a raw material composition, wherein the shell-sheets are dried by irradiation of a medium wavelength infrared ray before they are joined by the pair of die rolls, the shell-sheets used herein are each dried by a single-sided drying, in which the shell-sheet positioned on the casting drum is irradiated with a medium wavelength infrared ray to thereby dry mainly the one surface of the shell-sheet corresponding to outside of a capsule, to form into a sheet-form having an almost uniform thickness, an appropriate viscosity, and moisture content and enhanced adhesiveness between mutual sheets; and the filling is supplied to the shell-sheets in time for joining the shell-sheets at a segment section temperature of 35 to 50° C. without applying excessive heat load to a capsule filling to perform encapsulation, wherein the drying of the shell-sheets occurs prior to the encapsulation.

2. The method for manufacturing a soft capsule according to claim 1, wherein the wavelength of the medium wavelength infrared ray to be applied for drying the shell-sheet is 0.8 to 4.0 μm.

3. The method for manufacturing a soft capsule according to claim 1, wherein the shell-sheet is dried by medium wavelength infrared irradiation up to a moisture content of 19 to 29% at a stage of feeding between the pair of die rolls.

4. The method for manufacturing a soft capsule according to claim 1, wherein the shell portion in a liquid state before drying contains 5 to 25 parts by weight of λ carrageenan, 0.5 to 10 parts by weight of a metal salt, 3 to 100 parts by weight of dextrin, 20 to 80 parts by weight of a plasticizer, and 90 to 160 parts by weight of water relative to 100 parts by weight of starch.

5. The method for manufacturing a soft capsule according to claim 1, further containing κ carrageenan and τ carrageenan so as to satisfy a ratio of λ carrageenan: κ carrageenan: τ carrageenan=1:0.1:0.1 to 1:0.8:0.2.

6. An apparatus for manufacturing a soft capsule containing a filling coated with a shell portion formed of a shell-sheet, comprising:

a sheet molding section forming the shell-sheet having an almost uniform thickness from a molten shell material, a capsule molding section joining shell-sheets supplied between a pair of die rolls so as to face each other by butt joint function of the pair of die rolls having a molding projection, and a filling supply section supplying a filling to the shell-sheets in time for joining the shell-sheets, wherein the sheet molding section comprises a spreader box ejecting a molten shell material in the form of sheet having an almost uniform thickness and a casting drum cooling the shell-sheet ejected from the spreader box, the sheet molding section is further provided with a dryer equipped with a medium wavelength infrared heater; the shell-sheets are irradiated with a medium wavelength infrared ray from the heater to thereby obtain an almost uniform thickness, an appropriate viscosity, and moisture content; and the sheets of this state are fed to the capsule molding section, wherein the dryer is configured to dry the shell-sheet by employing a single-sided drying, in which the shell-sheet placed on the casting drum is irradiated with a medium wavelength infrared ray to thereby dry mainly the one surface of the shell-sheet, wherein the wavelength of the medium wavelength infrared ray applied from the medium wavelength infrared heater of the dryer to the shell-sheet is 0.8 to 4.0 μm, and wherein the dryer dries the shell-sheet prior to encapsulation of the capsule.

7. A method for manufacturing a soft capsule containing a filling within a shell portion formed of a shell-sheet, comprising ejecting a molten shell material in the form of a sheet having an almost uniform thickness from a spreader box, and cooling the shell-sheet ejected from the spreader box by a casting drum, and supplying shell-sheets thus obtained between a pair of die rolls so as to face each other, joining the shell-sheets by butt joint function of the die rolls, and supplying the filling from a segment in a filling supply section between the shell-sheets in time for joining, wherein the shell portion is formed by blending starch, λ carrageenan, a metal salt, dextrin, a plasticizer, and water as components for a raw material composition, wherein the shell-sheets are dried by irradiation of a medium wavelength infrared ray before they are joined by the pair of die rolls, the shell-sheets used herein are each dried by double-sided drying, in which the shell-sheet is removed from the casting drum and taken out in a transport path, in which the medium wavelength infrared ray is separately applied to each of the surfaces to thereby dry both surfaces of the shell-sheet, to form into a sheet-form having an almost uniform thickness, an appropriate viscosity, and moisture content and enhanced adhesiveness between mutual sheets; and the filling is supplied to the shell-sheets in time for joining the shell-sheets at a segment section temperature of 35 to 50° C. without applying excessive heat load to a capsule filling to perform encapsulation, wherein the drying of the shell-sheets occurs prior to the encapsulation.

8. The method for manufacturing a soft capsule according to claim 7, wherein the shell-sheet is dried by medium wavelength infrared irradiation in at least two stages and both surfaces of the shell-sheet are dried by irradiating one of the surfaces of the shell-sheet separately in each stage.

9. The method for manufacturing a soft capsule according to claim 7, wherein the wavelength of the medium wavelength infrared ray to be applied for drying the shell-sheet is 0.8 to 4.0 μm.

10. The method for manufacturing a soft capsule according to claim 7, wherein the shell-sheet is dried by medium wavelength infrared irradiation up to a moisture content of 19 to 29% at a stage of feeding between the pair of die rolls.

11. The method for manufacturing a soft capsule according to claim 7, wherein the shell portion in a liquid state before drying contains 5 to 25 parts by weight of λ carrageenan, 0.5 to 10 parts by weight of a metal salt, 3 to 100 parts by weight of dextrin, 20 to 80 parts by weight of a plasticizer, and 90 to 160 parts by weight of water relative to 100 parts by weight of starch.

12. The method for manufacturing a soft capsule according to claim 7, further containing κ carrageenan and τ carrageenan so as to satisfy a ratio of λ carrageenan: κ carrageenan: τ carrageenan=1:0.1:0.1 to 1:0.8:0.2.

13. An apparatus for manufacturing a soft capsule containing a filling coated with a shell portion formed of a shell-sheet, comprising:
 a sheet molding section forming the shell-sheet having an almost uniform thickness from a molten shell material,
 a capsule molding section joining shell-sheets supplied between a pair of die rolls so as to face each other by butt joint function of the pair of die rolls having a molding projection, and
 a filling supply section supplying a filling to the shell-sheets in time for joining the shell-sheets,
 wherein the sheet molding section comprises a spreader box ejecting a molten shell material in the form of sheet having an almost uniform thickness and a casting drum cooling the shell-sheet ejected from the spreader box,
 the sheet molding section is further provided with a dryer equipped with a medium wavelength infrared heater; the shell-sheets are irradiated with a medium wavelength infrared ray from the heater to thereby obtain an almost uniform thickness, an appropriate viscosity, and moisture content; and the sheets of this state are fed to the capsule molding section,
 wherein the dryer is configured to dry the shell-sheet by employing a double-sided drying, in which the shell-sheet is removed from the casting drum and taken out in a transport path, in which the medium wavelength infrared ray is separately applied to each of the surfaces to thereby dry both surfaces of the shell-sheet,
 wherein the wavelength of the medium wavelength infrared ray applied from the medium wavelength infrared heater of the dryer to the shell-sheet is 0.8 to 4.0 μm, and
 wherein the dryer dries the shell-sheet prior to encapsulation of the capsule.

14. The apparatus for manufacturing a soft capsule according to claim 13, wherein
 when the double-sided drying is performed by taking out the shell-sheet separately from the casting drum to the transport path and supplying air toward the irradiation surface of the shell-sheet from an upstream side to a downstream side in the sheet transport direction, and a support is provided so as to support the shell-sheet from below.

* * * * *